United States Patent [19]

Sedlacek et al.

[11] Patent Number: 4,479,934

[45] Date of Patent: Oct. 30, 1984

[54] METHOD AND AGENT FOR THE THERAPY OF IMMUNOCOMPLEX DISEASES

[75] Inventors: Hans-Harald Sedlacek; Friedrich R. Seiler, both of Marburg an der Lahn, Fed. Rep. of Germany

[73] Assignee: Behringwerke Aktiengesellschaft, Marburg an der Lahn, Fed. Rep. of Germany

[21] Appl. No.: 101,645

[22] Filed: Dec. 10, 1979

[30] Foreign Application Priority Data

Dec. 11, 1978 [DE] Fed. Rep. of Germany ....... 2853453

[51] Int. Cl.³ .................... A61K 39/00; A61K 37/04; A61K 39/395
[52] U.S. Cl. ...................................... 424/85; 424/177
[58] Field of Search ...................... 424/85, 86, 87, 88, 424/92, 177; 124/101

[56] References Cited

PUBLICATIONS

Chemical Abstracts, vol. 82, p. 361, Abst. No. 84193u, "Interaction of Antibodies, Complement Components and Various Cell Types in Immunity Against Viruses and Pyogeneic Bacteria", 1975.
Chemical Abstracts, vol. 79, p. 318, Abst. No. 30333j, Eden et al., "Mechanism of Binding Soluble Immune Complexes to Lymphocytes", 1973.
Chemical Abstracts, vol. 79, p. 318, Abst. No. 30334k, Yoshino et al., "Neutralization of Herpes Simplex Virus, VI, Mode of Action of Complement Upon Antibody-Sensitized Virus", 1973.
Chemical Abstracts, vol. 84, p. 260, Abst. No. 56290w, Masson et al., "Analysis of Biological Fluids", 1976.
Chemical Abstracts, vol. 84, p. 260, Abst. No. 56291x, Masson et al., "Analysis of Biological Fluids", 1976.
Nisonoff et al., Arch. Biochem. Biophys., vol. 89, p. 230, (1960).
Sedlacek et al., Behring Institute Mitteilungen, vol. 64, p. 78, (1979).
Sedlacek, Klin. Wochenschr., vol. 58, pp. 543, 593, (1980).
Haakenstad et al., Biology of Immune Complexes in "Autoimmunity", Ed. by Talal, Academic Press, (1977), pp. 278–350.
Porter, Biochem. J., vol. 73, p. 119, (1959).
Haupt et al., Klinische Wochenschryt, vol. 47, p. 270, (1969).
Nisonoff et al., Arch. Biochem. Biophys., vol. 89, p. 230, (1960).

*Primary Examiner*—Blondel Hazel
*Attorney, Agent, or Firm*—Curtis, Morris & Safford

[57] ABSTRACT

What is disclosed is a method for the therapy of immunocomplex diseases with an agent which contains Fc-reagents that react with the Fc-part of the antibody contained in the immunocomplex, but which themselves do not posses an immunologically active Fc-part or an Fc-part capable of being activated.

1 Claim, No Drawings

METHOD AND AGENT FOR THE THERAPY OF IMMUNOCOMPLEX DISEASES

Immunocomplexes are formed by the fixation of antigens on antibodies. Depending on the quantitative ratio of antigens to antibodies, immunocomplexes of different composition are formed, i.e. such with an excess of antigens, such within the equivalence range or such with an excess of antibodies.

The fixation of the antibody immunologically modifies (activates) the Fc-part of the antibody. Such immunologically modified Fc is capable of activating complement, of aggregating thrombocytes and of attaching itself to leucocytes. The fixation of Fc on thrombocytes or leucocytes provokes the release of mediators from these cells. Complement activation and the release of mediators, on the other hand, provoke inflammatory diseases which, with participation of the coagulation system, may proceed with formation of thromboses. Such inflammations may occur extravasally or intravasally, for example in the kidney or in the blood vessels of the extremities. In the kidney, they lead to the feared glomerulo-nephritis. Extravasally, they may lead, for example in the joints, to rheumatoid arthritis. Furthermore, immunocomplexes may fix, with the Fc-part of the participating antibodies, on lymphocytes and so reduce the immuno-reaction of the patient and thereby inhibit his resistance. These various diseases provoked by immunocomplexes are called immunocomplex diseases. The pathophysiology and the occurrence of immunocomplex diseases are described in detail and clearly arranged in Report No. 606 of the WHO.

The present possibilities for the therapy of immunocomplex diseases are limited. Symptomatically, substances are administered which reduce the inflammatory reaction (for example, corticoids) or immunosuppressors are administered which reduce the formation of antibodies so that fewer immunocomplexes are formed, or the immunocomplexes are removed from the blood circulation by plasmaphoresis. Another possibility for the therapy of immunocomplex diseases comprises the administration of antibodies which are directed specifically against the antigen contained in the immunocomplex. Such a therapy is intended to facilitate the ability of the immunocomplexes to be phagocytized and therewith their elimination. However, this is possible only if the phagocytizing system is still capable of absorption, i.e. if it is not diseased or already over-saturated. Another disadvantage is the fact that in most cases the antigen provoking the disease is unknown or that specific antibodies against the respective antigen are lacking or available to a limited degree only.

Now, we have found that, surprisingly, Fc-reagents can inhibit complement activation, the aggregation of thrombocytes and the fixation of leucocytes by immunocomplexes. Furthermore, they reduce the nephrotoxicity of immunocomplexes and are therefor utilizable for the therapy of immunocomplex diseases.

Fc-reagents are complement factors such as C1q, C3b or C3d or antibodies which react directly or indirectly with the immunologically modified (activated) Fc-part of the antibody contained in the immunocomplex. A precondition for the use of antibodies as Fc-reagents is, however, that they themselves do not contain a Fc-part which is immunologically active or capable of being activated.

Accordingly, the invention relates to an agent and method for the therapy of immunocomplex diseases containing one Fc-reagent or a mixture of Fc-reagents which react directly or indirectly with the Fc-part of the antibody contained in the immunocomplex and which themselves do not possess an immunologically active Fc-part or a Fc-part which is capable of being activated.

Such Fc reagents are, for example the complement factors C1q, C3b or C3d. They may also be antibodies which, because of their immunological specificity, react directly or indirectly with the immunologically modified (activated) Fc of antibodies in immunocomplexes, which antibodies however, themselves do not contain an immunologically active Fc-part or a Fc-part capable of being activated.

Antibodies without an immunologically active Fc-part are, for example enzymatic fission products of immunoglobulins such as $F(ab)_2$ or Fab fragments like those obtained, for example, by treating immunoglobulins with pepsin (Porter: Biochem. J. 73, 119, 1959) or with plasmin (Haupt, Heide: Klin. Wschr. 47, 270, 1969). However, antibodies with a chemically inactivated Fc-part, for example those treated by sulfitolysis (Schultze, Heremanns: Molecular Biology of Human Proteins, page, Elsevier Amsterdam, 1966) may also be used.

Antibodies which react directly with the immunologically modified (activated) Fc of antibodies in immunocomplexes because of their immunological specificity are, for example, rheumatoid factors as those occurring in various diseases, or antibodies obtained by the immunization of animals with immunoglobulins containing immunologically modified (activated) Fc. Such immunoglobulin preparations used for immunization are, for example antigen-antibody-immunocomplexes, or immuno-globulin aggregates or fission products of immuno-globulins which still contain immunologically modified (activated) Fc-parts, such as the Fc-part obtained after enzymatic fission of the immuno-globulin with papain (Porter: Biochem. J. 73, 119, 1959), plasmin (Haupt, Heide: Klin. Wschr. 47, 270, 1969) or pepsin (Porter 1959; Nisonof et al.: Arch. Biochem. Biophys. 89, 230, 1960).

However, antibodies may also be used according to the invention which, because of their specificity, react indirectly with immunologically modified (activated) Fc of antibodies in immunocomplexes, for example antibodies which react with complement factors which attach to the Fc-part of immuno-globulins in immunocomplexes such as antibodies against C1q, C3b or C3d.

For therapy, the preparation of the invention should be administered parenterally, for example i.m., i.v. or s.c. Local administration is also possible. For local or parenteral administration, the preparation of the invention is brought into a formulation known to the expert. The dose should be 1 ng to 1 g of protein per kg of body weight per administration.

The following examples illustrate the invention:

EXAMPLE 1

The complement activating activity of immunocomplexes of different composition, with and without treatment with a preparation according to the invention, was determined in the test according to Kabat and Majer (Experimental Immunochemistry, 2. Edition, Thomas Springfield). The results are shown in Table 1.

TABLE 1

Complement activating activity of immunocomplex samples, after treatment with an agent according to the invention for the therapy of immunocomplex diseases (in %)

| Treatment of the immunocomplexes (0.5 ml) with | Immunocomplexes with excess of antigens | Immunocomplexes at equivalence point | Immunocomplexes with excess of antibodies | Immunoglobulin aggregates |
|---|---|---|---|---|
| Control treated with physiol. salt solution (0.1 ml) | 100% | 100% | 100% | 100% |
| Rabbit-antibody (F(ab)$_2$-fragment against papain-Fc; 0.1 ml; 1% strength; 24 h, 4° C.) | 75% | 44% | 41% | 90% |
| Rheumatism factor (F(ab)$_2$-fragment; 0.1 ml; 1% strength; 24 h, 4° C.) | 70% | 44% | 50% | 86% |
| Clq (0.1 ml; 0.2% strength; 3 h, 40° C.) subsequently with rabbit antibody (F(ab)$_2$-fragment) against Clq (0.1 ml; 1% strength 24 h, 4° C.) | 20% | 15% | 14% | 53% |
| Clq (0.1 ml, 0.2% strength 3 h, 4° C.) | 21% | 25% | 22% | 30% |

The results clearly show that the treatment of immunocomplexes of different composition (with excess antigen or antibody or at the equivalence point) or also of immunoglobulin aggregates with a preparation according to the invention leads to a distinctly reduced complement activation.

EXAMPLE 2

The thrombocyte-aggregating activity of immunocomplexes, with and without treatment with a preparation according to the invention, was determined in a test according to Born (Nature 194, 927, 1962). The results are listed in Table 2.

TABLE 2

Thrombocyte-aggregating activity of immunocomplexes after treatment with a preparation according to the invention for the therapy of immunocomplex diseases (in %)

| Treatment of the immunocomplexes with: | Thrombocyte aggregation (quantitative ratio as in Example 1). |
|---|---|
| Control (treated with physiological salt solution) | 100% |
| Rabbit-antibody-(F(ab)$_2$-fragment) against papain-Fc | 80% |
| Rheumatism factor (F(ab)$_2$-fragment) | 80% |
| Clq, subsequently with rabbit-antibody (F(ab)$_2$-fragment) against Clq | 0% |
| Clq | 56% |

The results clearly show the inhibition of thrombocyte aggregation by a preparation of the invention.

EXAMPLE 3

The fixation of immunocomplexes, with or without treatment with a preparation of the invention, on Fc-receptors of lymphocytes was determined by the rosette test according to Seiler et al. (Z. f. Immunitätsforschung 155, 62, 1978). For this purpose, immunocomplexes were prepared from human erythrocytes and antibodies against human erythrocytes according to the publication by Seiler et al. (Behring Inst. Mitt. 52, 26, 1972) and their fixation on mouse leucocytes (insolated from spleen cells, Seiler et al., 1972) was determined by the so-called rosette test (details cf. Seiler et al. 1972).

The results are shown in Table 3.

TABLE 3

Inhibition of the fixation of immunocomplexes on Fc-receptors of leucocytes by a preparation of the invention

| Treatment of immunocomplexes with | Inhibition of the immunocomplex fixation |
|---|---|
| Control treated with physiological salt solution | 0 |
| Clq 0.01% | 17% |
| 0.025% | 44% |
| 0.05% | 56% |

The results clearly show the inhibition of the fixation of immunocomplexes on Fc-receptors of leucocytes by a preparation of the invention.

EXAMPLE 4

Immunocomplexes were injected intravenously into mice on three successive days and two hours after the last injection a preparation according to the invention was administered. 24 hours later the animals were sacrificed and the immunocomplexes were proved in the glomeruli of the kidney by immuno-fluorescence-histological methods and determined semi-quantitatively by dilution of the fluorescene-labeled antiserum used for the proof (details as to this method, cf. Sedlacek et al., Zeitschrift f. Immunitätsforschung 155, 61, 1978). The results are shown in Table 4.

TABLE 4

Inhibition of the deposition of immunocomplexes in the kidneys of mice by a preparation of the invention.

| After administration of immunocomplexes Treatment with: | Inhibition of the deposition of immunocomplexes in the kidney |
|---|---|
| Control (physiological salt solutions) | 0 |
| | 50 |

TABLE 4-continued

Inhibition of the deposition of immunocomplexes in the kidneys of mice by a preparation of the invention.

| After administration of immunocomplexes Treatment with: | Inhibition of the deposition of immunocomplexes in the kidney |
|---|---|
| Rabbit antibody (F(ab)$_2$-fragments) against papain Fc | |
| C1q | 60 |

The results clearly show the decrease in the deposition of immunocomplexes in the kidney after treatment of the animals with a preparation of the invention.

What we claim is:

1. A method for treating an immunocomplex disease in a patient suffering from such a disease, which method comprises locally or parenterally administering to said patient an effective amount of at least one Fc-reagent which reacts directly or indirectly with the Fc-part of the antibody contained in the immunocomplex causing said immunocomplex disease, said Fc-reagent itself not having an Fc-part which is immunologically active or capable of being activated, said Fc-reagent being selected from the group consisting of the complement factors C1q, C3b, and C3d; an antibody which reacts with any of said complement factors C1q, C3b, and C3d; F(ab)$_2$-fragments or Fab-fragments of an antibody, obtained by enzymatic fission of the antibody; antibodies, the Fc-part of which has been inactivated by chemical modification; antibodies which are rheumatoid factors; and antibodies produced by the immunization of an animal with immunoglobulin or with a fragment of immunoglobulin having an immunologically-modified activated Fc-part.

* * * * *

UNITED STATES PATENT AND TRADEMARK OFFICE
CERTIFICATE OF CORRECTION

PATENT NO. : 4,479,934

DATED : October 30, 1984

INVENTOR(S) : Sedlacek et al.

It is certified that error appears in the above-identified patent and that said Letters Patent is hereby corrected as shown below:

Column 4, last line, (Table 4, right column, last line), delete "50".

Column 5, line 8, (Table 4, right column, above "60"), insert --50--.

Signed and Sealed this

Fourth Day of June 1985

[SEAL]

Attest:

DONALD J. QUIGG

Attesting Officer     Acting Commissioner of Patents and Trademarks